(12) United States Patent
Coste-Maniere et al.

(10) Patent No.: US 9,486,159 B2
(45) Date of Patent: Nov. 8, 2016

(54) DEVICE AND METHOD FOR SUPERIMPOSING PATTERNS ON IMAGES IN REAL TIME, PARTICULARLY FOR GUIDANCE BY LOCATION

(71) Applicant: Intuitive Surgical Operations, Inc., Sunnyvale, CA (US)

(72) Inventors: Eve Coste-Maniere, Nice (FR); Thierry Vieville, Mougins (FR); Fabien Mourgues, Cannes (FR)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 50 days.

(21) Appl. No.: 14/215,915

(22) Filed: Mar. 17, 2014

(65) Prior Publication Data

US 2014/0275975 A1 Sep. 18, 2014
US 2016/0296137 A9 Oct. 13, 2016

Related U.S. Application Data

(63) Continuation of application No. 13/299,676, filed on Nov. 18, 2011, now Pat. No. 8,712,125, which is a continuation of application No. 12/908,298, filed on Oct. 20, 2010, now Pat. No. 8,086,008, which is a continuation of application No. 10/557,790, filed as application No. PCT/FR2004/001166 on May 13, 2004, now Pat. No. 8,126,223.

(30) Foreign Application Priority Data

May 22, 2003 (FR) ...................................... 03/06176

(51) Int. Cl.
*G06K 9/00* (2006.01)
*A61B 5/06* (2006.01)
(Continued)

(52) U.S. Cl.
CPC ........... *A61B 5/066* (2013.01); *A61B 1/00009* (2013.01); *A61B 5/055* (2013.01);
(Continued)

(58) Field of Classification Search
CPC .................. G06T 19/006; G06T 2007/10004; G06T 2200/04; G06T 2207/30196; G06T 7/0044; G06T 7/0051; G06T 15/005; G06T 15/60; G06T 2200/24; G06T 2207/10116; G06T 2207/30008; G06T 7/0012; G06T 7/004
See application file for complete search history.

(56) References Cited

U.S. PATENT DOCUMENTS 5,417,210 A * 5/1995 Funda ................ A61B 1/00193
348/65
5,782,762 A 7/1998 Vining
(Continued)

FOREIGN PATENT DOCUMENTS

CA 2067209 A1 4/1991
CA 2509727 A1 7/2004
(Continued)

OTHER PUBLICATIONS

European Search Report for Application No. EP10150348, mailed on Dec. 9, 2010, 4 pages.
(Continued)

*Primary Examiner* — Anand Bhatnagar

(57) ABSTRACT

The invention relates to a device for superimposing known patterns, characteristic of a region, on (real) images of said region. The device comprises, a memory in which patterns are stored, which are representative of a selected region, of known position and orientation with relation to a common reference and processing means, for determining a pattern representative of the selected portion in the memory, on receipt of the designation of at least one portion of an observed image of the selected region, taken at a selected angle and at least one representative attribute of said region, taking account of the attribute selected, then superimposing the determined pattern on the selected portion of the image taking account of the selected angle.

18 Claims, 2 Drawing Sheets

Figure 1:
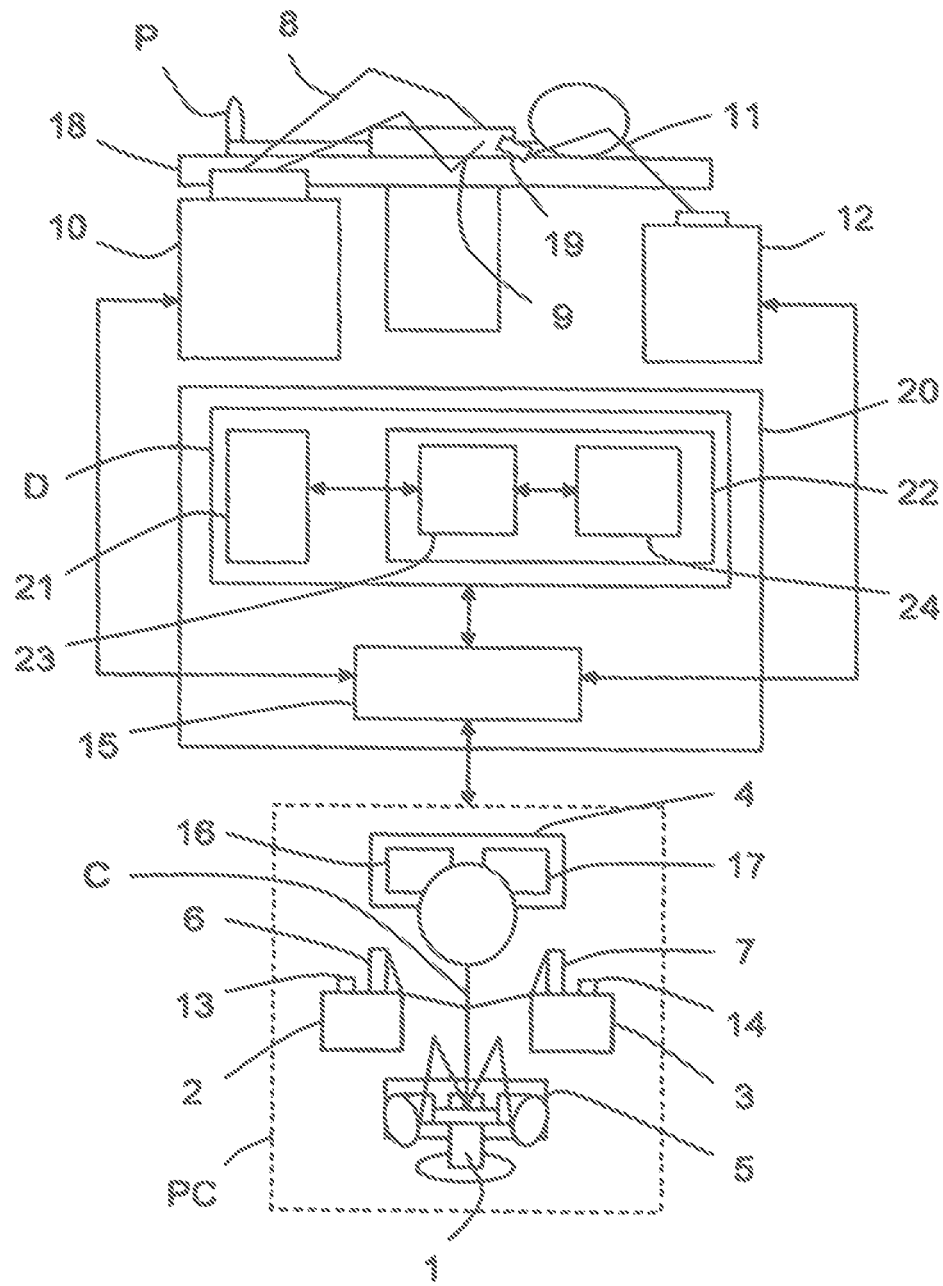

(51) Int. Cl.
*G06T 7/00* (2006.01)
*A61B 1/00* (2006.01)
*A61B 5/055* (2006.01)

(52) U.S. Cl.
CPC ............ *A61B 34/30* (2016.02); *G06T 7/0024* (2013.01); *G06T 2207/10068* (2013.01); *G06T 2207/10072* (2013.01); *G06T 2207/20092* (2013.01); *G06T 2207/30048* (2013.01); *G06T 2207/30101* (2013.01); *Y10S 128/922* (2013.01)

(56) References Cited

U.S. PATENT DOCUMENTS

| | | | | |
|---|---|---|---|---|
| 6,167,145 | A * | 12/2000 | Foley | G06F 19/321 |
| | | | | 382/128 |
| 6,301,495 | B1 * | 10/2001 | Gueziec et al. | A61B 6/00 |
| | | | | 600/407 |
| 6,480,732 | B1 | 11/2002 | Tanaka et al. | |
| 6,563,941 | B1 * | 5/2003 | O'Donnell | G06T 3/4061 |
| | | | | 382/131 |
| 6,681,129 | B2 * | 1/2004 | Matsuzaki | A61B 1/0005 |
| | | | | 600/407 |
| 7,321,673 | B2 * | 1/2008 | Watai | G06F 19/321 |
| | | | | 382/128 |
| 7,343,036 | B2 * | 3/2008 | Kleen | A61B 1/00009 |
| | | | | 382/128 |
| 7,356,178 | B2 | 4/2008 | Ziel et al. | |
| 7,366,562 | B2 | 4/2008 | Dukesherer | |
| 7,466,848 | B2 | 12/2008 | Metaxas et al. | |
| 7,570,791 | B2 * | 8/2009 | Frank | A61B 6/4441 |
| | | | | 382/128 |
| 7,606,861 | B2 * | 10/2009 | Killcommons | G06F 17/30067 |
| | | | | 382/128 |
| 7,702,137 | B2 * | 4/2010 | Dwyer | G06F 2/06 |
| | | | | 382/128 |
| 7,720,520 | B2 * | 5/2010 | Willis | A61B 5/0422 |
| | | | | 111/111 |
| 8,086,008 | B2 | 12/2011 | Coste-Maniere et al. | |
| 8,126,223 | B2 | 2/2012 | Coste-Maniere et al. | |
| 8,712,125 | B2 | 4/2014 | Coste-Maniere et al. | |
| 2003/0000535 | A1 | 1/2003 | Galloway et al. | |
| 2003/0158477 | A1 * | 8/2003 | Panescu | A61B 5/0422 |
| | | | | 600/424 |
| 2005/0089205 | A1 | 4/2005 | Kapur et al. | |
| 2007/0055142 | A1 * | 3/2007 | Webler | A61B 5/06 |
| | | | | 600/425 |
| 2009/0290771 | A1 | 11/2009 | Frank et al. | |
| 2010/0195919 | A1 | 8/2010 | Coste-Maniere et al. | |
| 2012/0130167 | A1 | 5/2012 | Coste-Maniere et al. | |

FOREIGN PATENT DOCUMENTS

| | | |
|---|---|---|
| CA | 2510494 A1 | 7/2004 |
| WO | WO-0124536 A2 | 4/2001 |

OTHER PUBLICATIONS

Hedley N.R., et al., "Explorations in the Use of Augmented Reality for Geographic Visualization" Presence MIT Press USA, 2002, vol. 11 (2), pp. 119-133.

PCT/FR04/01166 International Search Report, dated Mar. 2, 2005, 4 pages.

Shahidi, Ramin et al., "Implementation, Calibration and Accuracy Testing of an Image-Enhanced Endoscopy System," IEEE Transactions on Medical Imaging, 2002, pp. 1524-1535, vol. 21—Issue 12, IEEE.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Written Opinion for Application No. PCT/FR04/01166, mailed on Mar. 2, 2005, 5 pages (EVE1/PCT).

* cited by examiner

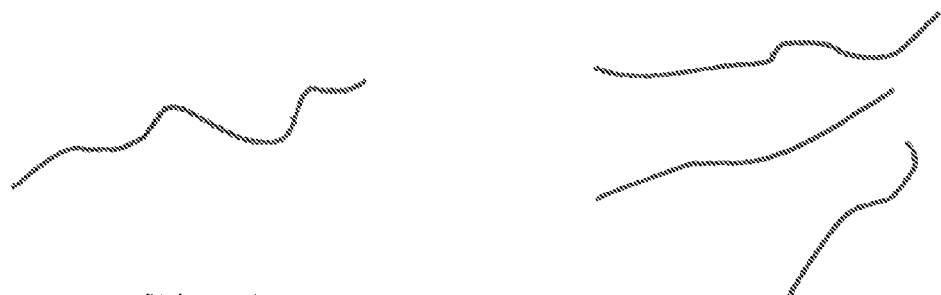
FIG.2
FIG.3
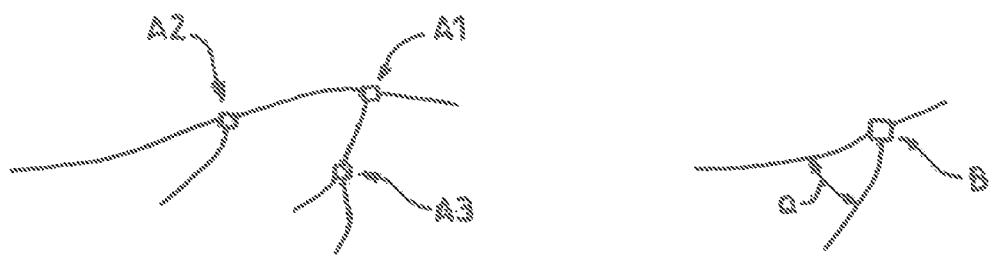
FIG.4
FIG.5
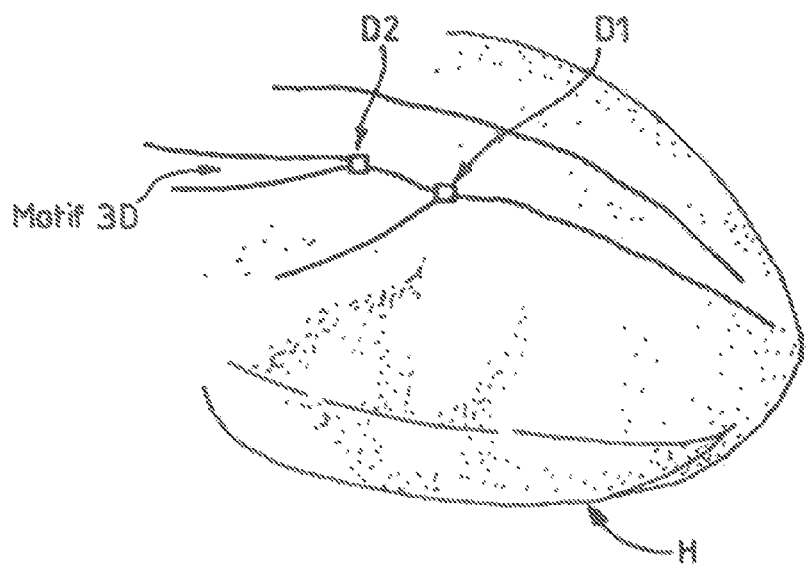
FIG.6

DEVICE AND METHOD FOR SUPERIMPOSING PATTERNS ON IMAGES IN REAL TIME, PARTICULARLY FOR GUIDANCE BY LOCATION

The invention relates to the field of image data processing, and more precisely to the real-time registration of data images representing known patterns on observation images.

In a number of fields, it is important to know precisely, at each instant, how one is positioned relative to a location or an object, or more generally a region.

This is the case for example in the field of surgery, particularly when it involves the so-called "mini-invasive" technique. In this case, the operating field is observed by an endoscopic camera introduced into the patient's body and delivering images to one or more monitors (or observation spectacles) at which a surgeon is positioned. In the case of a robot-assisted procedure, the surgeon remotely controls the robot manipulator arms of which the ends are also introduced into the patient's body. This applies in particular is to the Da Vinci® installation of Intuitive. Surgical Inc which includes, on one hand, a stereoscopic display device, giving the surgeon a three-dimensional (3D) view of the operating region, and on the other hand, manual control handles and pedals enabling the surgeon to address handling instructions and commands to the robot.

This operating technique is particularly beneficial for the patient in that it is minimally invasive. However, it is particularly awkward to put into effect by the fact that it only offers the surgeon, on one hand, a partial and to some extent distorted view of the region in which he/she is required to operate, due to the utilization of an endoscopic camera, and on the other hand, a very confined operating space that is encumbered by the robot manipulator arms and the endoscopic camera. Moreover, given that certain regions, such as the heart, are animated, the difficulty of the intervention is thereby accentuated.

To improve the situation, it has been proposed to implement a pre-operative modeling phase. In such a preoperative phase, a three-dimensional, and possibly temporal, model of the region to be operated on is constructed using images obtained by medical imaging. In the case of a heart, the coronary network is also determined with the aid of angiographic sequences, then this coronary network is overlaid onto the surface of the heart obtained by MRI. An anatomical model of the part of the patient's body containing the region to be operated on is then created, again using images obtained by medical imaging.

The optimal incision points are then determined, on one hand, taking into account the anatomical model and parameters such as the dexterity and the accessibility of the target region, and on the other hand, the optimal configuration of the robot arms, so as to avoid collisions and to obtain maximum separation, in particular.

On completion of the pre-operative phase, the surgeon can proceed with the operation. The patient is then placed on the operating table, then the endoscope is calibrated using a grid placed on the operating table and observed from different points of view. The patient's body is then incised at the optimal incision points previously determined. The robot arms are then positioned in the optimal configuration previously determined, and their ends, together with the tip of the endoscopic camera, are introduced into the patient's body via the incisions. The operation can then begin.

Despite the pre-operative phase, the surgeon may still experience difficulty in precisely locating the intervention area. This can occur particularly in the case of an intervention on an organ such as the heart. It may in effect be difficult to locate the interventricular artery due to an excess of fat at the surface of the epicardium. It is also possible to confuse the marginal branch of the circumflex artery or the diagonal branch (particularly developed) with the interventricular artery due to the high magnification of the endoscopic camera and/or the small field of view and/or the limited available perspective and/or poor positioning of the opening made in the pericardium.

Added to these difficulties in locating the operating targets, the surgeon can also encounter difficulties in positioning the endoscopic camera and therefore in estimating the angle at which the operating region is observed. Furthermore, given the lack of tactile feedback, it is not possible to identify the area to be operated on by pressing on it with the ends of the robot arms.

To sum up, the surgeon can experience real difficulty in determining the precise position of the area (or portion) of the observed region in which he/she must operate, relative to the known positions of the ends of the surgical robot arms.

To further improve the situation, it has been proposed to assist the surgeon by superimposing on the endoscope images of the observed region a pattern representing an element characteristic of the portion of the region where the operation has to be carried out, or an adjacent portion. These patterns are pre-extracted from digital models generated from images obtained by medical imaging. However, such assistance is not sufficient, particularly when the intervention region includes several substantially identical characteristic elements (either naturally, or by virtue of the observation angle), as in the case of the coronary network.

Similar difficulties in pinpointing the precise position of locations or objects, via portions of real images, also arise in other technical fields, and particularly in the field of urban guidance.

The object of the invention is therefore to remedy all or some of the aforementioned drawbacks.

To this end a device is proposed for superimposing known patterns (for example three-dimensional (3D) patterns), characteristic of a region, on (real) images of this region in real time.

This device is characterized in that it includes, on one hand, a memory in which are stored patterns representing portions of a selected region and of known position and orientation relative to a common reference, and on the other hand, processing means for determining a pattern representative of the designated portion in the memory, on receipt of the designation of at least one portion of an observed image of the selected region, taken at a selected angle, and at least one representative attribute of this portion, taking account of the designated attribute, then superimposing the determined pattern on the designated image portion taking account of the selected angle.

The device according to the invention may include other characteristics which may be taken separately or in combination, and particularly:

processing means capable of performing the registration by successively designating portions of observation images of the selected region and/or attributes representing these portions, a memory capable of storing a three-dimensional model representing the region within the selected reference. In this case, the processing means are preferably designed to perform the registration(s) in particular using the stored three-dimensional model, processing means capable of determining at least one measurement equation from the designation of an image portion, an attribute and at least one hypothesis, and of determining the pattern and its registration as a function of the determined measurement equation. Several measurement equations can be determined from the designation of several image portions, attributes and hypotheses. In this case, the processing means determine the pattern and its registration as a function of a combination of the determined measurement equations. The registration is of the rigid type, for example, by minimization of a selected criterion, taking account of the measurement equations derived from the hypotheses. Furthermore, the hypotheses can be transmitted to the processing means by the user making the designations, or can be directly determined by the processing means, processing means capable of supplying image data representative of a registered pattern so that it can be observed at the same time as the observation images, in superimposed fashion, on the corresponding designated image portion, once the registration has been done, a memory capable of storing a correspondence table between the patterns and information data representing them. In this case, the processing means are advantageously designed to provide, whenever they are instructed to do so, information data representing a registered pattern, processing means capable of providing, substantially at the same time and whenever they are instructed to do so, image data representing a registered pattern and the information data representing this pattern.

The invention also relates to an installation for guidance by location including, in a first part, observation means capable of providing images of a selected region at a selected angle, in a second part, a display device (for example one or more computer monitors or observation spectacles) enabling these images to be displayed, in a third part, a man/machine interface enabling a user to designate at least one portion of the region represented by the displayed images and at least one attribute representing this portion, and in a fourth part, a registration device of the type described above, furnished with portion(s) and attribute(s) designated by the man/machine interface and delivering image data representing a registered pattern so that the latter is superimposed by the display device on the designated portion displayed, once the registration has been performed.

The observation means may include acquisition means, for example of the endoscope type, the position of which is known at each instant relative to a calibration reference, from which the position of the observed region is defined, and capable of delivering observation images to the display device.

When the installation is used for guidance only, for example urban guidance, it preferably includes control means designed, when they receive a request designating a pattern of the observed region, to instruct the registration device to determine position data representing the position of this pattern in relation to the calibration reference, taking account of the registration, then of specifying control instructions intended to guide the user to the portion matching this pattern.

When the installation is used for surgical interventions, it can include a surgical robot incorporating arms whose respective positions in relation to the calibration reference are known at each instant and which can be remotely controlled by instructions provided by a user via the man/machine interface. However, it also includes control means linked to the registration device and to the man/machine interface, and designed, when they receive a request designating a pattern of the observed region, on one hand, to instruct the registration device to determine position data representing the position of this pattern in relation to the calibration reference taking account of the registration, and on the other hand, to specify control instructions intended to move the robot arms in the vicinity of the portion of the region matching the designated pattern.

The invention also relates to a process for real-time registration of known patterns (for example 3D), characteristic of a region, onto images of this region, and consisting of:

storing in a memory patterns representing portions of a selected region and of known position and orientation relative to a common reference, observing the selected region at a selected angle and delivering observation images of this region in real time, designating at least one portion of the observation image of the selected region and at least one attribute representing this portion, identifying in the memory a pattern representing the designated portion, taking into account the designated attribute, and overlaying the pattern on the designated image portion taking the selected angle into account.

The method according to the invention may include other characteristics. which may be taken separately or in combination, and particularly:

the registration may be performed by successively designating portions of observation images of the selected region and/or attributes representing these portions, a 3D model representing the region in the selected reference may be stored in the memory, and each registration may be performed at least from this 3D model, a rigid type registration may be performed, by minimization of a selected criterion. In this case, at least one measurement equation is preferably determined from the designation of an image portion, an attribute and at least one hypothesis, and the pattern is determined and the rigid registration is performed as a function of the determined measurement equation. Several measurement equations can be determined from the designation of several image portions, attributes and hypotheses, constituting the constraints, and the pattern can be determined and its rigid registration performed as a function of a combination of the determined measurement equations. At least some of the hypotheses can be transmitted by the user making the designations, for example in the form of attributes, image data representing a registered pattern can be provided so that it is observed at the same time as the observation images, and in a superimposed fashion, on the corresponding designated image portion, a correspondence table between the patterns and information data representing these patterns can be stored in the memory, and information data representing a pattern can be delivered on request, image data representing a registered pattern can be displayed, the designations can be performed via a man/machine interface, when a request is received from a user designating a pattern contained in the observed region, position data representing the position of this pattern can be determined in relation to the calibration reference (from which the position of the observed region is defined), taking the registration into account, and control instructions intended to guide the user to the portion corresponding to said designated pattern can then be determined, provision can be made for a surgical robot incorporating arms the respective positions of which in relation to the selected reference are known at each instant and can be remotely controlled by instructions supplied by a user via the man/machine interface, and when a user request is received designating a pattern of the selected region, position data representing the position of the pattern can be determined in relation to the calibration reference, taking the registration into account, and control instructions intended to move the robot arms in the vicinity of the portion of the region matching the designated pattern can, then be determined.

Other features and advantages of the invention will become apparent upon examination of the following detailed description together with the attached drawings in which:

FIG. 1 is a diagrammatic illustration of an embodiment of an installation according to the invention suitable for application in the field of mini-invasive telesurgery, FIG. 2 is a diagrammatic illustration of a 3D pattern representing a coronary artery, FIG. 3 is a diagrammatic illustration of a 3D pattern representing three adjacent coronary arteries, FIG. 4 is a diagrammatic illustration of a 3D pattern representing a coronary artery and three bifurcations, FIG. 5 is a diagrammatic illustration of a 3D pattern representing an angular sector at a bifurcation between two coronary arteries, and FIG. 6 is an image of a heart onto which a 3D model has been superimposed, after registration.

The attached drawings may not only serve to complement the invention, but may also contribute to its definition, as the case may be.

The invention relates in a general manner to real-time registration of image data representing known patterns, for example three-dimensional patterns (3D), characteristic of a region, onto observation images of this region. However, it also relates to location guidance installations using registration of this kind, such as for example urban guidance and telesurgery systems, particularly of the "mini-invasive" type.

Reference will first be made to FIG. 1 in describing a non-restrictive embodiment of an installation according to the invention suitable for mini-invasive telesurgery.

The telesurgery installation illustrated is for example composed of the Da Vinci® installation of Intuitive Surgical Inc. Schematically, it includes a control station CS including a chair 1 enabling a surgeon S to sit at a console equipped with a control keyboard (not shown), a first manual control 2 for the left hand, a second manual control 3 for the right hand, a display device 4, in this instance of the stereoscopic type, and a set of control pedals 5.

Each manual control 2, 3 includes for example a control lever 6, 7 (of the "joystick" type) intended to control one of the manipulator arms 8, 9 of a robot 10, which will be described below, and the manipulator arm 11 of a stereoscopic camera 12, which will also be described below, and one or more control keys 13, 14 (of the touch-sensitive type, or pushbutton type, or "mouse" type).

The set of pedals 5 includes for example a pedal enabling a manual control 2, 3 to be assigned to control the surgical robot 10, a pedal enabling a manual control 2, 3 to be assigned to control the camera 12, and a pedal enabling a manual control 2, 3 to be assigned to control an installation control module 15, which will be described below.

The control keyboard, the manual controls 2 and 3, and the set of control pedals 5 constitute a man/machine interface.

The display device 4 includes, in this instance, a first screen 16, for the display of real two-dimensional (2D) images delivered by a first channel of the camera 12 and intended for the left eye of the surgeon S. and a second screen 17, for the display of real two-dimensional (2D) images delivered by a second channel of the camera 12 and intended for the right eye of the surgeon S.

The surgical robot 10 is intended to be placed in proximity to the operating table 18, on which the patient P is placed for the mini-invasive operation. It generally includes two manipulator arms 8 and 9 equipped with ends adapted to the operation and intended to be introduced into the body of the patient P via incisions.

The stereoscopic camera 12 includes a manipulator arm 11 the end of which carries two endoscopic optical fibers 19 defining two image acquisition channels.

The surgical robot 10 and the endoscopic camera 12 can be combined to form a "master robot".

The installation additionally includes a control unit 20, for example arranged in the form of a workstation, including the control module 15 and a registration device according to the invention D, which will be further described below. The control module 15 is linked to the console of the control station CS, to the surgical robot 10, to the stereoscopic camera 12 and to the registration device D.

The registration device D, according to the invention, is intended in a general manner to overlay known patterns, which are characteristic of a region (in this instance where an operation is to be carried out), onto (real) images of this region in real time. In the following description, it is considered that the patterns are three-dimensional (3D), but they can be two-dimensional (2D), at least in some instances.

This device D firstly includes a memory 21 storing three-dimensional (3D) patterns representing characteristic portions of the region in which the operation is to take place, and of known position and orientation relative to a common reference (or pre-operative reference). The device D also includes a processing module 22 linked to the memory 21 and designed, when it receives the designations, on one hand, of at least one portion of an observation image of the intervention region, taken at a selected angle by the endoscopic camera 12 and delivered by the control module 15, and on the other hand, of at least one attribute representing the designated portion, to determine in the memory 21 a 3D pattern representing this designated portion, taking account of the designated attribute and the selected viewing angle, and then to superimpose the determined 3D pattern on the designated image portion.

It is important to note that a set of 3D patterns may constitute a 3D model. Therefore, the registration may apply not only to a 3D pattern, but also to a 3D model.

In the case of the heart, for example, a 3D model may represent the coronary tree, this 3D model then being composed of a multiplicity. of 3D patterns representing structures characteristic of the coronary tree, such as arteries, junctions and bifurcations for example. In fact, in the case of a coronary tree, two types of structures are defined. A first type includes curves representing the arteries, while a second type includes characteristic elements, such as junctions or bifurcations for example. These different types are illustrated in FIGS. 2 to 5.

More precisely, FIG. 2 illustrates a pattern representing a coronary artery, FIG. 3 illustrates a pattern representing a configuration of three coronary arteries, FIG. 4 illustrates a pattern representing a configuration of three bifurcations on a coronary artery, and FIG. 5 illustrates a pattern representing an angle a characteristic of a bifurcation between two coronary arteries.

For example, a bifurcation is defined, in a first part, by an index (integer identifying the bifurcation), in a second part, by two indexes (Art1 and Art2 which identify the two arteries concerned), and in a third part, by a point (triplet of coordinates of the bifurcation in the pre-operative reference). Similarly, an artery is defined, on one hand, by an index (integer identifying the artery) and, on the other hand, by a set of parameters of a B-spline constituting the center line of the artery (quadruplet (xi, yi, zi, ui) in which (xi, yi, zi) is a triplet defining each control point of the artery in the pre-operative reference, and ui denotes a node of the B-spline of which the value is between 0 and 1).

As the generation of 3D patterns is not the object of the invention, it will not be described here in detail. A precise description of a mode of generating these patterns is for example given in the paper by Eve Coste-Manière et al "Optimal Planning of Robotically Assisted Heart Surgery: Transfer Precision in the Operating Room", B. Siciliano and P. Dario (Eds.): Experimental Robotics VIII, STAR 5, pp. 424-434, 2003, or in the paper by Fabien Mourgues et al "3D+t Modeling of coronary artery tree from standard non simultaneous angiograms": Proc. of MICCAI, Volume 2208 of LNCS, Springer (2001), 1320-1322.

It is simply noted that the generation of 3D patterns of an intervention region, such as for example an organ like the heart, first requires three-dimensional, and possibly temporal (3D+t), modeling of the intervention region from images obtained by medical imaging (MRI, scanner, etc). For example, in the case of a heart, a volumetric (3D) model of the heart can be obtained by MRI at a given instant in the cardiac cycle. To obtain a complete 3D+t model, the volumetric (3D) model is animated from a 3D+t model of the coronary network of the modeled heart, obtained from sequences of angiogram images (X rays), also referred to as coronarograms, taken at different angles and over several cycles, and synchronized relative to an electrocardiogram (ECG).

In the foregoing example of a 3D model of a coronary tree, the 3D patterns are therefore fractions (or portions) characteristic of the 3D coronary tree (or network) of which the positions are known in relation to the volumetric (3D) model of the heart of the patient P.

The pre-operative reference against which the positions of the 3D patterns and the heart are defined is normally that of the outer envelope of the patient P. It is effectively in relation to this outer envelope that the surgical robot 10 and the endoscopic camera 12 can be calibrated. Furthermore, the fact that the position of the heart, and therefore its coronary network, is related to the outer envelope makes it possible to register the patient in relation to the robot in the operating room.

A 3D anatomical model of the patient's body is also determined, at least in an extensive part containing the region to be operated on, again based on images obtained by medical imaging.

The positions, orientations and configurations of the 3D patterns (and the models) are therefore stored in the memory 21 relative to a common reference defined by means of index marks placed on the outer envelope of the patient P.

Preferably, the 3D model of the heart of the patient P, and the 3D anatomical model, are also stored in the memory 21.

As the object of the invention does not include the pre-operative planning phase of the surgical operation, this will not be described here. Therefore, the following description deals with the application of the device D according to the invention, within an installation according to the invention, in the operating phase.

It will simply be noted that the pre-operative planning phase, which is optional only, has the object in particular of determining the three optimal incision points that will allow the ends of the manipulator arms 8, 9 and 11 of the surgical robot 10 and the endoscopic camera 12 to be inserted, taking into account the 3D anatomical model of the body of the patient P, and parameters such as the dexterity and the accessibility of the target region. It also involves determining the optimal configuration of the manipulator arms 8 and 9 of the surgical robot 10 to avoid collisions and to obtain maximum separation.

The device D operates within the installation once the arm 11 and the camera 12 (endoscopic as the case may be) have been calibrated. This involves determining precisely the optical parameters of the camera and its position in the reference system of the arm 11. An example of a method of endoscopic calibration is described in the paper by F. Mourgues et al "Flexible calibration of actuated stereoscopic endoscope for overlay in robot assisted surgery", Proc. of MICCAI, Volume 2488 of LNCS, Springer (2002), 25-34. The calibration data are preferably stored in a memory of the control module 15.

Incisions are then made in the body of the patient P. at the optimal incision points determined during the preoperative planning phase. The manipulator arms 8 and 9 of the surgical robot 10 and the arm 11 of the endoscopic camera are then placed in the optimal configuration, also determined during the pre-operative planning phase, and their respective ends are introduced into the body of the patient P via the incisions. It is to be noted that the determination of the optimal incision points is a preferred option, but not obligatory, it being possible for the positioning of the robot arms and the endoscope to be determined empirically by the surgeon.

The two channels of the endoscopic camera 12 deliver their respective sequences of 2D images to the control module 15, Which transmits them to the display device 4 so that they are displayed on the screens 16 and 17. The surgeon S can then observe the region in which the object of the operation, namely the heart H, is located, at the observation angle of the endoscopic camera 12. FIG. 6 is an image of the heart H of the type observed by the surgeon S on the screens 16 and 17.

Knowing the intervention region, it is possible at the start of the operation to propose a first overlay of the 3D model (in this instance the coronary tree) onto the displayed observation images. This can be done manually or by external registration of the patient placed on the operating table with the patient's pre-operative model. External registration involves first using the robot end to point at several radio-opaque markers pre-attached to the patient's thorax, and previously segmented in the scanner images. The rigid transformation between the pointed markers and the segmented markers is then computed. This initial rigid transformation serves to accomplish the transfer from the pre-operative reference (reference in which the patterns of the 3D model to be registered are represented) to the robot base reference, and to the endoscopic camera reference (using the calibration of the endoscope in this case). This external registration technique is described in particular in the paper by E. Coste-Manière et al "Optimal planning of robotically assisted heart surgery: Transfer precision in the operating room, B. Siciliano and P. Dario, eds, Springer Tracts in Advanced Robotics, Experimental Robotics VIII, Volume 5, Springer (2002), 424-434.

Once the external registration, if any, has been done, the zone where the intervention is to take place is precisely identified. To do this, the surgeon S designates at least one portion of the images displayed on the screens 16 and 17 and at least one attribute representing each image portion, via the man/machine interface. The designation of a portion is effected for example by selecting the portion on the image, with a mouse. The designation of an attribute is effected either by a voice command, or by selection from a list displayed on the screens 16 and 17 or on an auxiliary screen. In the example illustrated in FIG. 4, the squares A1 to A3 mark the points . where the surgeon S "clicks" with his/her mouse to designate three portions of the region that appear to him/her to be significant. Similarly, in the example illustrated in FIG. 5, the square B marks the point where the surgeon S "clicks" with his/her mouse to designate the portion of the region that appears to him/her to be significant.

The attributes are standard information (or classes) each of which describes a known local characteristic or a known local configuration, or in a general manner any information enabling the processing module 22 of the device D to determine the matching 3D pattern in the memory 21.

Once in possession of designations supplied by the surgeon S. the device D transmits them to its processing module 22, so that it determines in the memory 21 a 3D pattern which appears to it to be representative of the designated portion(s), taking account of the designated attribute(s).

This determination is performed by an extraction module 23 linked to the memory 21. The processing module 22 must then perform the registration of this pattern (and the whole of the 3D model of which it is part, as the case may be). This involves determining how to orient and position the pattern so that it can be superimposed on the portion designated by the surgeon, taking account of the angle at which the intervention region is observed by the endoscopic camera.

The registration is preferably performed by a registration module 24 of the processing module 22. Furthermore, this registration is preferably rigid, by minimization of a criterion constructed from the measurement equations. The measurement equations are derived in this instance from hypotheses supplied by the surgeon, when he/she thinks he/she recognizes a portion, such as an artery or a bifurcation between known arteries for example, or are determined directly by the registration module 24. Of course, another type of registration can be envisaged, particularly affine registration.

For example, rigid registration involves determining at least one measurement equation from the designation of an image portion, an attribute and at least one hypothesis on the identity of the pattern determined by the extraction module 23. This registration may also take into account the 3D model of the heart when this is stored in the memory 21.

Several measurement equations can be determined from the designation of several image portions, several attributes and one or more hypotheses, which constitute a corresponding set of constraints. In this case, the registration module 24 generates several sets of equations corresponding to the different possible hypotheses and then optimizes the registration parameters by minimizing a criterion. It then classifies the registrations obtained as a function of their relevance and selects the best registration. The parameter estimating method is described in particular in the paper by T. Vieville et al "Implementing a multi-model estimation method", The International Journal of Computer Vision, 44 (2001), 41-64.

However, any other known parameter estimation technique can be used.

Once the rigid registration of the 3D pattern is done, it is possible to register the whole of the 3D model of which said pattern forms a part. Thus, it is the whole 3D model, viewed at the observation angle of the endoscopic camera, and not only the determined and registered 3D pattern, which can be superimposed onto the displayed or observed image. Of course, certain portions of the 3D model may not be visible due to the observation angle.

The processing module 22 can then transmit to the control module 15 the position data of the registered 3D pattern (or of the entire 3D model of which it forms part), in the (calibration) reference of the image displayed (or observed, when the surgeon is equipped with observation spectacles), and the image data which define this 3D pattern (or model), thereby instructing the display device 4 to display it in a superimposed fashion on the observation images delivered by the endoscopic camera 12 (or observed through the spectacles).

An overlay of an extensive 3D pattern on an image of the heart is depicted in FIG. 6. The squares D1 and D2 mark the places where the surgeon S has clicked with the mouse to designate two portions of the intervention region which appear to him/her to be significant, and the portion of the coronary network superimposed on the image of the heart H represents the 3D pattern registered by the device D.

By virtue of this overlay, the surgeon knows immediately how he/she is positioned relative to the area that is to be operated on.

In certain situations, the designations made by the surgeon S may not enable the extraction module 23 to determine the 3D pattern which corresponds to the selected portion, or to enable the registration module 24 to perform a suitable registration, thereby producing an incorrect overlay of the 3D pattern (or model) on the displayed image. Therefore, the processing module 22 can be arranged so as to determine precisely the position of the observed region in the reference by successive registrations each based on the extraction of a new 3D pattern following the designation of at least one other observation image portion, and at least one attribute representing this other portion.

In this situation, two cases can be envisaged. In a first case, the 3D pattern determined by the extraction module 23 is not superimposed on the image of the observed region in the portion selected by the surgeon S, or the registered 3D pattern is superimposable but does not correspond to the structure observed by the surgeon on the selected portion. The surgeon must then make a new designation to cause the registration operation to converge. In a second case, it is the control module 15 that automatically notices the error and which sends a message to the surgeon requesting fresh designations.

On receipt of these new designations, the registration device D repeats the processing described above, taking into account the new and old designations. In particular, when set up for this purpose, it can compute new hypotheses and measurement equations.

It can also be envisaged to store in the memory 21 a correspondence table between the 3D patterns and information data representing them. This may include for example the pattern name, such as for example the name of an artery and/or its branches if any, or the coordinates of a target point, or operating data recorded in the planning phase, such as the identification of a stenosis or a calcification zone for example.

In this case, the processing module 22 can be configured so as to deliver the information data associated with a 3D pattern (registered or not) when it receives the instruction to do so from the control module 15 (for example in case of a request by the surgeon S). However, an automatic mode of operation can also be envisaged wherein, each time the processing module 22 registers a 3D pattern and is preparing to deliver the related position and image data to the control module 15, it extracts the associated information data from the memory 21 so as to communicate it substantially simultaneously.

The control module 15 can be also designed, each time it receives a request designating a 3D pattern of the region observed, so as to, on one hand, instruct the registration device D to determine position data representing the position of this 3D pattern in relation to the calibration reference, taking account of the registration, and on the other hand, to determine control instructions intended to move the manipulator arms 8 and 9 of the surgical robot 10 to the vicinity of the portion of the region matching the designated 3D pattern.

The installation described above can be used for other types of operation, such as open liver or breast surgery for example. In a general manner, the installation according to the invention serves to guide the user in the accomplishment of his/her task in an environment where he/she has only a partial and/or distorted view, and/or in a difficult environment.

Furthermore, as previously indicated, the registration device D according to the invention can be used in applications other than those described above. It can be used in particular in installations designed solely for location guidance (without the intervention of a remotely-operated robot), particularly in urban areas.

It is thus possible to envisage an installation mounted in a road vehicle, and including one or more cameras delivering real images of the environment to a control module for display on screens installed in the driver's compartment, and a registration device D linked to said control module. The installation can be also connected to an on-board satellite guidance device, of the GPS type.

In this application, the registration device D stores in its memory patterns representing the environment (or region) in which the vehicle can move and determined from digital recordings made previously. These patterns, of which the positions are defined in a selected reference, are for example building facades, or notable buildings or sites, or statues, or works of art. The memory can also include a volumetric model of the environment, and a correspondence table between the patterns and data information on these patterns.

Once the cameras have been calibrated against a calibration reference, the installation can be used.

In this case, when the control module receives a request from a passenger in the vehicle designating a pattern of the observed region (selected from a list of stored patterns using a mouse or by pressing a touch-sensitive display screen), it instructs the registration device D to determine position data representing the position of this pattern in relation to the calibration reference, taking into account the adjustment resulting from discrepancies between the selected reference index and the calibration index, then to determine control instructions intended to guide the driver of the vehicle to the portion of the region corresponding to this pattern. As indicated above, the control module may rely on vehicle position data delivered by the GPS device to determine the control instructions, as the case may be. Once the vehicle has arrived at the designated location, the pattern can be superimposed onto the real image of the portion of the region, and information data associated with said pattern can be delivered to the passenger.

However, an automatic mode of operation can also be envisaged in which the registration device D receives from a passenger in the vehicle the designations of at least one observed and displayed portion of a region (selected using a mouse or by pressing the touch-sensitive display screen) and at least one attribute representing this portion, such as for example the nature of a building (house, school, city hall, museum, church) or a location (garden, park, square) or an object (statue, sculpture, work of art), and determines in its memory the pattern which best matches this designated portion, taking account of the designated attribute and the selected viewing angle. It then overlays the determined pattern onto the designated image portion. It then derives the position data of the registered pattern from the displayed image reference (calibration reference), and transmits this data together with image data defining this pattern and any associated information data to the control module which issues instructions for the data to be displayed on the screens, in a superimposed fashion, on the observation images delivered by the cameras. This mode of operation is therefore similar to that described previously in the surgical application.

A variant of the installation can also be envisaged that is adapted for location guidance of users traveling on foot in an environment, for example urban. In this case, the device according to the invention is advantageously mounted in communications equipment, 10. such as a mobile telephone for example, equipped with a location function, for example by triangulation or by GPS, and a camera, and an inertial reference system as the case may be.

The processing module 22 of the registration device D and the control module 15 of the installations can be made in the form of electronic circuits, software (or data processing) modules, or a combination of software modules and electronic circuits.

The invention also relates to a method for real-time registration of known patterns, characteristic of a region, onto images of this region.

The method can be implemented with the aid of the registration device and the installations described above. Given that the principal and optional functions and sub-functions provided by the steps of this method are substantially identical to those provided by the various means constituting the device and the installations, only the steps embodying the principal functions of the method according to the invention will be summarized below.

This method is characterized in that it involves:
  storing in a memory 21 patterns representing portions of a selected region and of known position and orientation relative to a common reference,
  observing the selected region at a selected angle and delivering observation images of this region in real time,
  designating at least one portion of the observation image of the selected region and at least one attribute representing this portion,
  identifying in the memory a pattern representing the designated portion, taking account of the designated attribute, and
  overlaying the pattern on the designated image portion taking the selected angle into account.

The invention is not limited to the embodiments of the device, installations and method described above by way of example only, but encompasses all variants that can be envisaged by the person skilled in the art pursuant to the claims that follow.

The invention claimed is:

1. An apparatus comprising:
   a memory storing an identity and data for each of a plurality of objects; and
   a processor configured to:
   receive an image of a viewed object;
   receive input from a user, said input comprising a designation of a portion of the image and a designation of the identity of the viewed object;
   register an object stored in the memory to the designated portion of the image based on the designated identity of the viewed object; and
   superimpose a visual representation of the data corresponding to the registered object on the image for display.

2. The apparatus of claim 1, the data comprising a 3-dimensional model of the corresponding object.

3. The apparatus of claim 2, the processor further configured to:
   receive an observation angle corresponding to the received image; and
   superimpose the visual representation of the 3-dimensional model of the corresponding object on the image based on the received observation angle.

4. The apparatus of claim 1, the designation of the identity of the viewed object comprising a nature of an object within the designated portion.

5. The apparatus of claim 1, the designation of the identity of the viewed object comprising a location of an object within the designated portion.

6. The apparatus of claim 1, designation of the identity of the viewed object comprising the name of an object within the designated portion.

7. The apparatus of claim 1, the image being received from an endoscope, the apparatus further comprising a robotic arm maneuverable within a field of view of the endoscope.

8. The apparatus of claim 7, the processor configured to register the object by successively positioning the robotic arm at predetermined locations to align a reference frame of the data with a reference frame of the image.

9. The apparatus of claim 1, the processor configured to register the data by minimizing a criterion constructed from at least one measurement equation.

10. The apparatus of claim 9, the at least one measurement equation derived from a hypothesis associated with the viewed object.

11. The apparatus of claim 1, the image being received from a camera mounted on a moving vehicle.

12. The apparatus of claim 1, the data comprising a three-dimensional model of a patient's heart, the image comprising a view of the patient's heart, the processor configured to superimpose a visual representation of a coronary tree of the model of the patient's heart on the image for display.

13. The apparatus of claim 1, the identity comprising an attribute describing a known local characteristic or known local configuration of a corresponding object.

14. A method comprising:
   receiving an image of a viewed object;
   receiving input from a user, said input comprising a designation of a portion of the image and a designation of the identity of the viewed object;
   registering an object stored in a memory to the designated portion of the image based on the designated identity of the viewed object; and
   superimposing a visual representation of data corresponding to the registered object on the image for display.

15. The method of claim 14, the data comprising a 3-dimensional model of the corresponding object.

16. The method of claim 14, further comprising:
   receiving an observation angle corresponding to the received image; and
   superimposing the visual representation of the 3-dimensional model of the corresponding object on the image based on the received observation angle.

17. The method of claim 14, the receiving the image comprising receiving the image from an endoscope, the method further comprising maneuvering a robotic arm within a field of view of the endoscope.

18. The method of claim 17, the registering the object comprising successively positioning the robotic arm at predetermined locations to align a reference frame of the data with a reference frame of the image.

* * * * *